United States Patent [19]

Lansing et al.

[11] Patent Number: 5,328,368

[45] Date of Patent: Jul. 12, 1994

[54] DENTAL CURE LIGHT COVER

[75] Inventors: Thomas A. Lansing, St. Paul, Minn.; Paul W. Kuehn, Eau Claire, Wis.

[73] Assignee: Pinnacle Products, St. Paul, Minn.

[21] Appl. No.: 871,271

[22] Filed: Apr. 20, 1992

[51] Int. Cl.⁵ .................... A61C 3/00; A61C 1/16
[52] U.S. Cl. ............................... 433/116; 433/29
[58] Field of Search ............... 433/29, 116, 229; 250/504 H

[56] References Cited

U.S. PATENT DOCUMENTS

| | | | |
|---|---|---|---|
| 3,552,558 | 1/1971 | Poncy | 206/63.2 |
| 3,732,975 | 5/1973 | Poncy | 206/63.2 |
| 3,847,280 | 11/1974 | Poncy | 206/306 |
| 4,136,776 | 1/1979 | Poncy | 206/306 |
| 4,165,000 | 8/1979 | Poncy | 206/306 |
| 4,723,912 | 2/1988 | Nieusma | 433/229 |
| 4,757,381 | 7/1988 | Cooper et al. | 433/116 |
| 4,907,968 | 3/1990 | Eisner et al. | 433/116 |
| 4,974,580 | 12/1990 | Anapliotis | 128/4 |

*Primary Examiner*—John J. Wilson
*Attorney, Agent, or Firm*—Merchant, Gould, Smith, Edell, Welter & Schmidt

[57] ABSTRACT

A disposable elongate protective sheath for covering the tip of a dental cure light to prevent cross contamination between dental patients.

5 Claims, 2 Drawing Sheets

DENTAL CURE LIGHT COVER

BACKGROUND OF THE INVENTION

1. Field of the Invention

The present invention relates to a protective and disposable cover for use with a dental cure light.

2. Description of the Prior Art

Cross contamination or exchange of biologic materials between dental patients has become an important issue in the practice of dentistry. During the course of dental procedures both the dentist and the patient come into contact with many objects capable of transporting bioburden. Many of these objects are either disposable or readily sterilized. The dental cure light does not fit into either of these categories. The typical dental cure light has complex and expensive interchangeable tips which are used inside the patients mouth and come into contact with saliva and other biologic materials.

Some commonly used dental products harden when exposed to light. It is common to apply these materials to teeth and to "expose" them with a hand held cure light. In use, the cure light tip is placed into the patient's mouth, while the handle of the cure light is held by the dentist. Most cure light units are equipped a removable cure light probe which may be removed from the light curing unit for cleaning.

Usually the dentist will be required to remove and carefully clean the tip between uses to prevent cross contamination between patients. The disposable cure light cover taught herein also prevents cross contamination between patients, without the requirement of cure light probe cleaning between patients.

The use of protective coverings for medical apparatus is well known. It is now common to provide protective sheaths for certain devices. See, for example:

U.S. Pat. No. 4,136,776 to Poncy which discloses a disposable sheath package for use with a thermometer. In use, this sheath is placed over the thermometer to prepare the thermometer for use.

U.S. Pat. No. 4,974,580 to Anapliotis which discloses a protective covering for use with an endoscope. This apparatus may be used for covering an illumination source and it includes an acrylic glass window.

SUMMARY OF THE PRESENT INVENTION

In the present invention, a disposable, transparent, flexible and deformable cover is provided for use with a dental cure light. Typically the dental light curing unit has a cylindrical light probe having a curve or bend to facilitate use within the patient's mouth. The cover of the present invention has an elongate tubular sheath portion which covers a substantial portion of the cure light probe. The protective cover also includes a reduced diameter distal portion which has a diameter smaller than the diameter of the cure light probe and which may be deformed to hold the cure light cover onto the cure light probe. The cure light cover is preferably dispensed and packaged between two paper release liners to keep the cover clean prior to use. The release liners are separated slightly by the user to insert the cure light probe. The user may grip the release liners and slide the cover into position over the cure light tip.

BRIEF DESCRIPTION OF THE DRAWINGS

Reference may be had to the following description of an exemplary embodiment taken in conjunction with the accompanying drawings in which identical reference numerals identify identical structure throughout the several figures of the drawing wherein.

DETAILED DESCRIPTION OF THE PREFERRED EMBODIMENT

Figure 1:
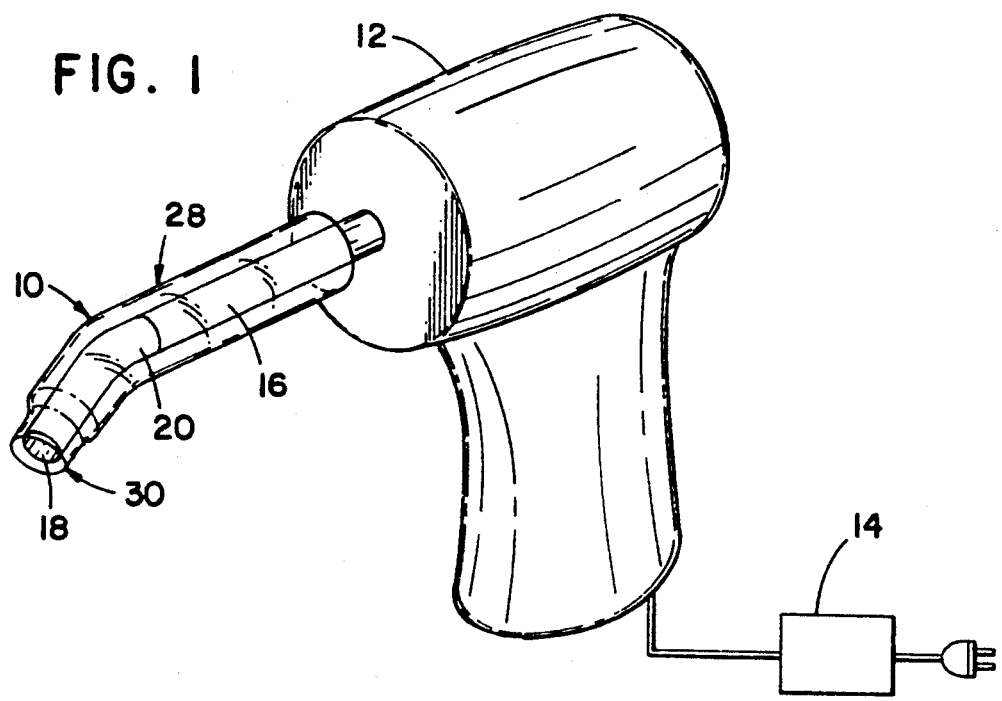
FIG. 1 is a perspective view of the light curing unit with a cure light cover placed into position and ready for use.

FIG. 1 is a perspective view showing the light cure unit 12 along with its controller 14. Typically a light bulb is placed within the light cure unit 12 and light is conducted through a light guide 16 to a removable and rotatable cure light probe 20. The light which exits the cure light tip 18 "exposes" the dental resin or other dental material. As shown in the drawing the cure light cover 10 is positioned over the light probe 20 with the distal tip portion 30 in conformity with the cure light tip 18. The sheath portion 28 fits loosely along the length of the cure light probe 20 and light guide 16 and extends to a position proximate the light cure unit 12. In general, the length of the sheath portion is sufficient to remain outside of the patient's mouth during use. This prevents material from the patient's mouth from entering the interior of the tubular cure light cover 10. The length of the distal tip portion 30 is just sufficient to reliably engage and conform to the cure light tip 18.

Figure 2:
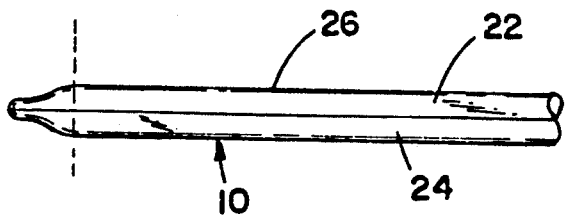
FIG. 2 is a side view of the cure light cover.

FIG. 2 shows the cure light cover 10 in isolation. The cure light cover 10 is substantially tubular in shape although it is preferably made from an upper ply 22 and a lower ply 24 which are Joined at a seam 26. During manufacture the seam 26 is formed by a heat forming die which joins the two plies.

Figure 3:
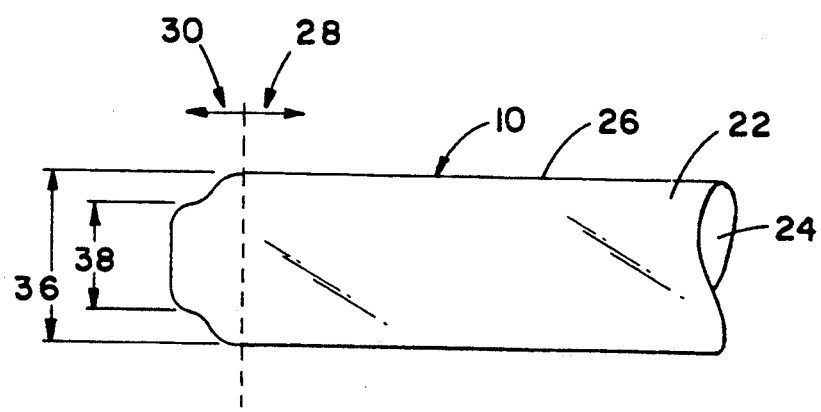
FIG. 3 is a top view of the cure light cover.

FIG. 3 shows a top view of the cure light cover 10 showing the elongate sheath portion 28, and the distal tip portion 30. In general, the sheath dimension 36 is sized to slide over the cure light probe 20, and it is slightly in excess of the diameter of the cure light probe 20 diameter. The distal tip dimension 38 is slightly less than the cure light probe 20 tip diameter so that the distal tip portion 30 of the cure light cover 10 can stretch and conform to the cure light tip 18. Since the cure light cover 10 is preferably formed and dispensed as a substantially planar structure the actual dimensions 36 and 38 will be approximately (Pi*D)/2, where D is the appropriate diameter of the cure light probe 20. At present, commercially available cure light probes are substantially circular in cross-section and are available in 3,8 13, and 14 mm (diameter) sizes. It should be apparent that the cover may be used with non round cure light probes should they become available.

Figure 4:
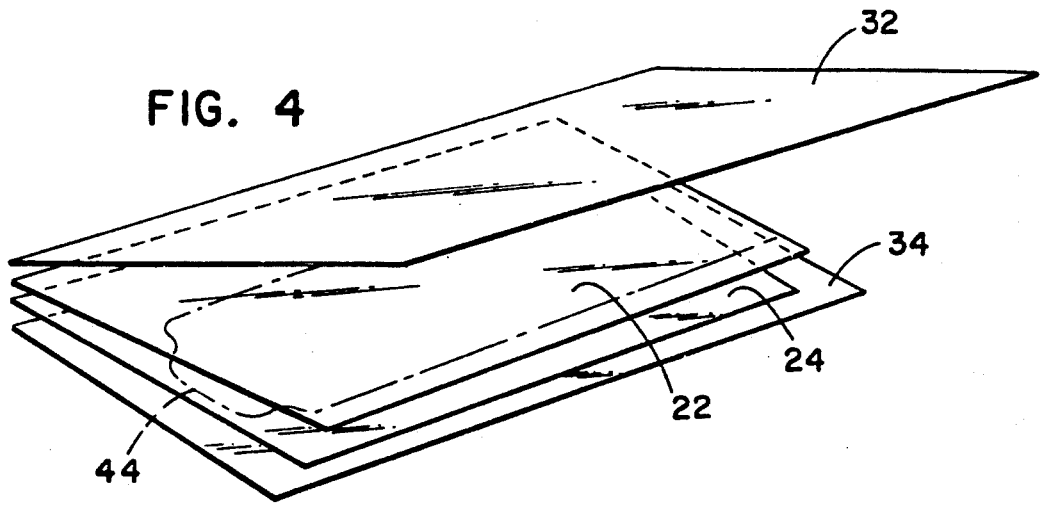
FIG. 4 is a perspective view of the various layers of the cure light cover and dispenser liners.

FIG. 4 schematically depicts the preferred process for forming the cure light cover 10 and the associated dispenser liners 32 and 34. Preferably polymeric films 22 and 24 are plied together between an upper release liner 32 and a lower release liner 34. A die is used to apply heat and pressure to the composite assembly to shape the profile 44 of the cure light cover 10. This process also forms the seam 26 between the upper ply 22 and the lower ply 24 and causes the profile 44 of the cure light cover 10 to be embossed on the entire assembly. This process bonds the polymeric films tightly together and gently adheres the cure light cover 10 to both the upper release liner 32 and the lower release liner 34.

Figure 5:
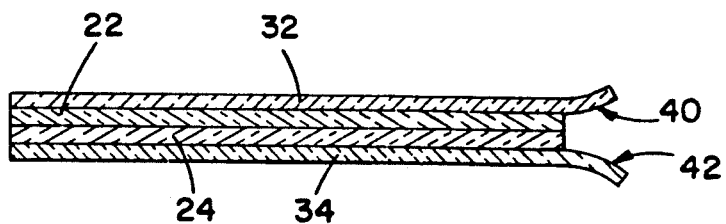
FIG. 5 is a cross-section of the cure light cover and the dispenser liners; and, FIG. 6 is a top view of the cure light cover and dispenser liners.

FIG. 5 shows the completed assembly in cross-section. It is preferred to have the upper release liner 40 overlap and extend beyond both the cure light cover 10 and the lower release liner 34. This geometry produces two user grip tabs 40 and 42 which facilitate fitting of the cure light cover 10 onto the cure light probe 20.

Figure 6:
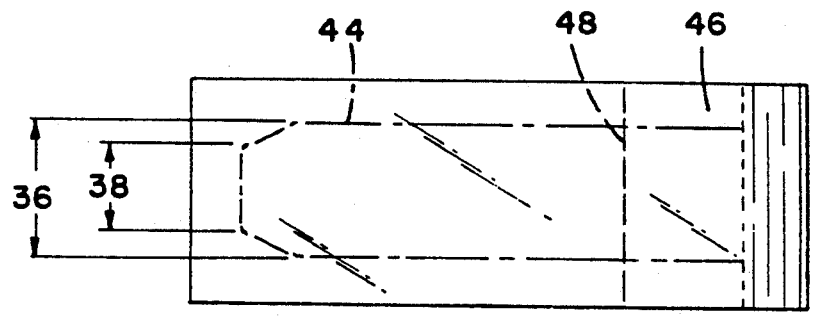

FIG. 6 shows a line of perforation 48 defining the grip area 46. Perforation of the release liners and cover 10, facilitate placement of the cover on the probe. In use the cover is slide onto the probe until it "bottoms out" on the cure light tip 18. Continued force applied to the grip area 46 separates the liner from the cover without puncturing the cure light cover 10.

An illustrative cover for a 8 mm light probe may be formed from ethylene methacrylate (EMA) film having an individual ply thickness of 0.001 inches. This material is sufficiently transparent to the light from the cure light probe and is readily heat sealed to form the seam 26. This material is also sufficiently tacky and deformable to reliably adhere the cure light cover 10 to the cure light probe 20 structure. Suitable dimensions 36 and 38 are 13 mm and 18 mm respectively.

What is claimed is:

1. A disposable single use protective cover apparatus for a dental cure light of the type having an approximately cylindrical distal light probe, said light probe having a nominal diameter, comprising:
    an elongate transparent polymeric substantially tubular sheath member having an effective diameter larger than said light source nominal diameter, and having a predetermined first length;
    a distal cover member, having a diameter smaller than said nominal light source diameter, and having a predetermined second length, forming a tubular distal cover member; and
    whereby, said tubular distal cover member is deformed into conformity with said distal light source by stretching said tubular distal cover member over said distal light probe.

2. The apparatus of claim 1 wherein said tubular sheath member and tubular distal cover member form a unitary structure formed from substantially planar films joined at a seam extending along the length of said elongate sheath.

3. The apparatus of claim 1 or claim 2 wherein said polymeric material is ethylene methacrylate film.

4. A disposable single use protective cover apparatus for a dental cure light of the type having an approximately cylindrical distal light probe, said light probe having a nominal diameter, comprising:
    an elongate transparent polymeric substantially tubular sheath member having an effective diameter larger than said light source nominal diameter, and having a predetermined first length;
    a distal cover member, having a diameter smaller than said nominal light source diameter, and having a predetermined second length, forming a tubular distal cover member; and
    whereby, said tubular distal cover member is deformed into conformity with said distal light source by stretching said tubular distal cover member over said distal light probe,
    an upper release liner;
    a lower release liner;
    said upper release liner and said lower release liner together forming a sheath reception area for positioning and protecting said sheath prior to use.

5. The apparatus of claim 4 further comprising:
    an upper grip tab formed on said upper release liner;
    a lower grip tab formed on said lower release liner;
    said upper grip tab and said lower grip tab together forming means for applying said sheath to said cure light tip.

* * * * *

UNITED STATES PATENT AND TRADEMARK OFFICE
CERTIFICATE OF CORRECTION

PATENT NO. :   5,328,368

DATED      :   July 12, 1994

INVENTOR(S) :  Thomas A. Lansing and Paul W. Kuehn

It is certified that error appears in the above-identified patent and that said Letters Patent is hereby corrected as shown below:

In column 1, line 18, before the word "mouth", please delete the word "patients", and insert therefor --patient's--

In column 1, line 25, after the word "equipped", please insert the word --with--

In column 2, line 39, please delete the word "Joined", and insert therefor --joined--

In column 3, line 16, please delete the word "slide", and insert therefor --slid--

Signed and Sealed this

Ninth Day of May, 1995

Attest:

BRUCE LEHMAN

Attesting Officer        Commissioner of Patents and Trademarks